United States Patent
Skalla et al.

(10) Patent No.: US 6,203,762 B1
(45) Date of Patent: *Mar. 20, 2001

(54) SURGERY PLUME FILTER DEVICE AND METHOD OF FILTERING

(75) Inventors: Randy Marc Skalla, Leesburg, GA (US); Carl Austin Ahrens, Cincinnati, OH (US); Robert Keith Garner, Jr., Miamisburg, OH (US); Bradley Carl Wilkinson, Cincinnati, OH (US)

(73) Assignee: EnviroSurgical, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,023

(22) Filed: Jun. 7, 1999

Related U.S. Application Data

(63) Continuation of application No. 08/657,156, filed on Jun. 3, 1996, now Pat. No. 5,910,291, which is a continuation-in-part of application No. 08/198,480, filed on Feb. 18, 1994, now Pat. No. 5,522,808, which is a division of application No. 07/851,862, filed on Mar. 16, 1992, now Pat. No. 5,288,469.

(51) Int. Cl.[7] .......................... B01D 50/00; B01D 53/00; A61L 9/00
(52) U.S. Cl. .......................... 422/171; 422/169; 422/170; 422/122; 96/134; 96/341; 261/DIG. 26
(58) Field of Search .................... 422/168–171, 422/4, 5, 122; 261/DIG. 26; 96/134, 150, 341, 178, 246, 253

(56) References Cited

U.S. PATENT DOCUMENTS

| | | |
|---|---|---|
| 2,379,338 | 6/1945 | Bingman ................................. 95/150 |
| 2,988,166 | 6/1961 | Klemm ................................... 96/341 |
| 3,286,444 | 11/1966 | Boswinkle et al. ..................... 96/246 |
| 3,482,377 | 12/1969 | Walrave ................................. 96/253 |
| 3,963,463 | 6/1976 | Huppke ................................. 96/178 |
| 3,969,479 | 7/1976 | Lonnes et al. ............................. 422/4 |
| 4,125,589 | 11/1978 | DeVries ............................... 423/210 |
| 4,238,461 | 12/1980 | DeVries ............................... 423/210 |
| 4,403,611 | 9/1983 | Babbitt et al. ......................... 604/73 |
| 4,425,143 | 1/1984 | Nishizawa et al. .................. 422/169 |
| 4,443,354 | 4/1984 | Eian ..................................... 502/401 |
| 4,604,110 | 8/1986 | Frazier ................................. 422/122 |
| 4,624,791 | 11/1986 | Ferriss ..................................... 95/92 |
| 4,772,273 | 9/1988 | Alchas ................................. 604/218 |
| 4,826,513 | 5/1989 | Stackhouse et al. .................... 96/124 |
| 4,963,134 | 10/1990 | Backscheider et al. ............... 55/467 |
| 4,986,839 | 1/1991 | Wertz ................................... 604/319 |
| 5,030,423 | 7/1991 | Obee et al. .......................... 422/122 |
| 5,039,319 | 8/1991 | Glass et al. ............................. 95/150 |
| 5,047,072 | 9/1991 | Wertz et al. ......................... 604/319 |
| 5,108,621 | 4/1992 | Robins ................................. 210/728 |
| 5,288,469 | 2/1994 | Skalla ................................. 604/218 |
| 5,910,291 | * 6/1999 | Skalla et al. ......................... 422/171 |

* cited by examiner

*Primary Examiner*—Hien Tran
(74) *Attorney, Agent, or Firm*—Wood, Herron & Evans, LLP

(57) ABSTRACT

A filter device and method of filtering components from a surgery plume. The filter device comprises an integral solution reservoir which intercepts an airstream passage and airstream and cooperates with the airstream to direct air and solution into pads to create a foam. The foam created by the pads and solution and additional elements of the filter react with one or more undesirable components of the surgery plume to cleanse the airstream prior to exhaustion into the atmosphere. No separate solution supply or delivery system is necessary.

10 Claims, 4 Drawing Sheets

SURGERY PLUME FILTER DEVICE AND METHOD OF FILTERING

CROSS REFERENCE TO RELATED APPLICATIONS

This application is a continuation of application Ser. No. 08/657,156 filed Jun. 3, 1996, now U.S. Pat. No. 5,910,291 which is a continuation-in-part of application Ser. No. 08/198,480 filed Feb. 18, 1994, now U.S. Pat. No. 5,522,808 which is a divisional of application Ser. No. 07/851,862 filed Mar. 16, 1992, which is now U.S. Pat. No. 5,288,469, both application and issued patent being incorporated by reference herein in their entireties.

FIELD OF THE INVENTION

The invention relates to a filtering device, and a method of filtering, for removing from an airstream particulates, various hazardous and odor causing chemicals and bacteria and virus. Specifically, the invention relates to a filter device for removing hazardous and odor causing species from an airstream generated in an operating room, such as by the surgical application of focused energy on tissue, as in electrocautery or laser surgery.

BACKGROUND OF THE INVENTION

It has been known for a number of years to utilize focused energy in the form of heat or electricity to burn or sear skin and underlying tissue in connection with the treatment of various ailments and disease. The practice, known as cauterization, has been particularly useful for the removal of abnormal skin growths. One drawback to the practice has been the generation of foul-smelling materials at the site resulting from the burning of the tissue. Fortunately, the volume of these materials was typically relatively low due to the type of ailments treated by the process. However, where electrocautery is used to seal blood vessels in connection with invasive surgery, the volume of materials generated is substantially increased.

Since the 1970's, lasers have been used in operating rooms to treat a wide variety of ailments. As in the traditional practice of cauterization, the laser was used to burn or sear tissue. However, because the laser was used in larger scale invasive surgery, the amount of materials generated at the site was substantially larger than that from traditional cauterization, with resulting problems related to the volume of the foul-smelling materials and the effect on operating room personnel.

The gas-generation problem has become more prevalent because in a number of surgical applications, lasers have an advantage over conventional scalpel cutting tools in that the laser is a more precise instrument, resulting in less trauma to adjacent tissue. Also, because the heat generated by the laser cauterizes the tissue as it is being cut, there is less blood loss and the healing process is speeded along.

In operation, the laser scalpel performs its cutting function by burning a narrow width of tissue. This process vaporizes moisture in the tissue and creates a smoke plume consisting primarily of water vapor, but which also includes small quantities of potentially hazardous and toxic gases, odor-causing gases, particulate matter, including those of 1 micron or less, and bacteria and viruses.

This smoke generated by the laser scalpel, otherwise known as the laser plume, creates a variety of problems for the surgical operating team. The laser plume obscures the view of the surgeon during cutting. Further, the plume eventually deposits a coating on the mirrors used for viewing the cutting site. The operating room personnel also risk contracting infection by inhaling bacteria and virus from the tissue vaporized by the laser which are carried in the plume. The materials generated by the laser scalpel and carried in the laser plume tend to cause headaches and nausea, and more rarely nosebleeds and vomiting, which in certain instances have forced the operation to be terminated due to the sickness of the personnel. Finally, it has recently been determined that low levels of mutagenic, carcinogenic and toxic agents such as cyanide, formaldehyde and benzene are carried along in the plume.

The volume of the generated laser plume is a function of the power of the laser scalpel. As higher powered lasers are used, increasing amounts of laser plume are generated, consequently increasing the risk and discomfort to the operating team. The major lasers used in the medical and surgical fields utilize the lasing materials Neodymium-Yttrium Aluminum Garnet (Nd:YAG), Carbon Dioxide and Argon.

Early attempts to address the problem of removing the laser plume involved the use of vacuum devices fitted with an activated charcoal filter. These early devices removed the laser plume smoke from the cutting site and improved the surgeon's view of the site. However, the vacuum device could not remove all of the plume generated by high energy laser scalpels. Also, the moisture in the plume would tend to deactivate the charcoal over a period of time. Further, the charcoal filter had little or no effect on reducing the odor.

To meet the new requirements caused by the use of higher powered lasers, LASE Inc., a subsidiary of U.S. Medical Corporation, Cincinnati, Ohio, developed a smoke evacuation system incorporating an activated charcoal filter, a moisture filter before the charcoal filter to prevent deactivation of the charcoal filter, a high efficiency particle absorbing filter for capturing particles as small as 0.12 micron, a larger diameter hose to capture the increased volume of laser plume generated, and a deodorizing cartridge to mask the odor created by the plume. One type of evacuator unit used in laser surgery was the Lase System, from U.S. Medical Corporation, and discussed in U.S. Pat. No. 4,963,134 which is incorporated herein by reference.

In the middle 1980's, clinical studies were conducted which determined that amounts of mutagenic and carcinogenic agents such as cyanide, formaldehyde and benzene, and also traces of compounds such as acetone, isopropanol, cyclohexane, and toluene, are produced during the laser surgery operation. Studies also recently determined that bacteria and viruses in the tissue subjected to laser were carried in the active state in the plume. Smoke evacuation systems employing only activated carbon and a particulate filter are unable to remove the mutagenic agents, bacteria and virus species, and the odor causing species from the plume. Rather, these systems were only able to partially mask the odor causing species in the plume.

The removal of mutagenic and carcinogenic agents and other agents, such as bacteria and odor causing species, from the surgery plume is addressed by a filter device and filtering method which utilize an oxidizing and surface active solution to contact the plume. The device and method are the subject of co-pending application Ser. No. 08/198,480 entitled Surgery Plume Filter Device and Method of Filtering and U.S. Pat. No. 5,288,469, which application and patent are commonly owned with the present application.

The filter device is connected in-line to an evacuation unit which draws a vacuum airstream for capturing the surgery plume. The solution is supplied to the filter device from an external solution source, and specifically is sprayed or pumped from the external source into the airstream being filtered to interact with the airstream and form a foam which continues to rupture or break up and refoam. The foam is contained in the filter device as the airstream flows therethrough, and the contact time of the surgery plume with the foam containing the surface active and oxidizing component is sufficient to break down the mutagenic and carcinogenic agents and odor causing species, and to kill the bacteria and virus in the surgery plume airstream. The filter further utilizes an activated carbon component, for further filtering, such as filtering of organic compounds.

While such filtering devices and methods are quite effective in cleansing a surgery plume of undesirable agents, it has been necessary to accommodate the filtering device with a specifically designed evacuation unit or filter cart. More particularly, such filter devices and methods require that oxidizing solution be introduced into the filtered airstream, and therefore, the evacuation units must include a supply of solution, transfer lines coupling the filter device with the solution supply, and a controlled pumping mechanism for delivering the solution to the filter device. As may be appreciated, the various solution supply components of the evacuation units are subject to wear and failure, and thus must be repaired or replaced. Since the filter requires the solution for proper operation, maintenance and replacement of the solution delivery components are necessary and increase the cost of using the filter. Furthermore, the evacuation units may have to be somewhat larger than conventional units to accommodate the additional equipment.

Additionally, many available evacuation units are designed to draw a vacuum through a dry filter and do not have the capability of delivering solution. Therefore, either the filter cannot be used or the evacuation unit must be retrofitted with a solution delivery system. Retrofitting is not only inconvenient for medical personnel, but improperly retrofitting an existing unit to operate with the filter device may reduce the filter device's effectiveness. As such, the necessity of providing a particular evacuation unit to use the filter device makes the device somewhat impractical and costly for both the manufacturer and suppliers and the end user.

Accordingly, it is an object of the invention to reduce the inconvenience of using a surgery plume filter device or method to remove certain agents from the airstream.

It is another objective to provide a filter device which is readily usable with a variety of different evacuation units or filter carts without retrofitting the particular evacuation unit or the filter device.

It is still another objective to provide a filter device and method that may be effectively utilized to remove harmful and offensive agents from a surgery plume without concern for the particular evacuation unit available or its liquid delivery capability.

It is still another objective to reduce or eliminate maintenance and replacement costs associated with solution by delivery systems used in conjunction with the filter device.

SUMMARY OF THE INVENTION

These objectives and other objectives are achieved by the present invention comprising a filter device and method which effectively cleanses an airstream having a surgery plume component without the need for a separate solution supply reservoir and components for delivering a charge of oxidizing solution into the filter device. In that way, the filter device and method of the invention may be readily and conveniently utilized with a variety of different evacuation units and filter carts. This reduces the inconvenience to medical personnel of matching a filter device with a particular cart or unit or retrofitting the existing unit or the filter device. Furthermore, a supplier only has to carry a single filter line to meet the needs of customers with a variety of different filter carts and evacuation units. Still further, repair and replacement costs associated with the solution delivery into the filter device are reduced or eliminated.

To that end, the filter device and filtering method of the present invention comprise a solution reservoir integrally formed within the filter device for automatic interaction with the airstream. The reservoir contains a measured amount or charge of the oxidizing solution to be utilized to form a foam to cleanse the surgery plume. When a vacuum is drawn through the filter device, the airstream automatically engages the reservoir and the solution therein. The airstream and solution impinge upon at least one dispersal pad, and the combination of the airstream, in-line solution, and pad creates a foam. The filter device of the invention does not require the separate introduction of a solution, and thus a separate supply reservoir and associated pump and solution lines are not necessary. As a result, the filter device may be utilized and the inventive method practiced using conventional evacuation units that do not include fluid delivering systems.

The filter device comprises an inlet port, an outlet port, and a passage therethrough for accepting and exhausting the airstream and surgery plume. The airstream passage intercepts the solution reservoir and the engagement between the airstream, solution and pad creates a foam which disperses preferably through a plurality of dispersal pads and into a foaming chamber. One or more of the pads are preferably coated with an active coating for the removal of one or more undesirable agents from the airstream, for example, aldehydes. In accordance with the principles of the invention, the foam is continually formed and broken down or ruptured inside the confined space of the filter device and is then reformed. The foam created by the integral reservoir is exposed to the airstream in and around the dispersal pads and foaming chamber for a time sufficient for the surface active and oxidizing components of the foam to break down the mutagenic and carcinogenic agents and odor causing species, and to kill the bacteria and virus in the surgery plume. Proper flow rates in the filter device are maintained to efficiently reduce and eliminate the undesirable agents while the flow pressure does not drop substantially from the inlet port to the outlet port. The discussion herein will use "surgery plume" to include not only the gaseous and particulate materials generated in electrocautery and laser surgery, but also the volatile bonding agents used in orthopedic procedures, bone tissue particles from cutting or drilling procedures, and the like.

Downstream of the foam are separate layers of a drying agent and activated carbon filter which respectively collect moisture and trap residual particulate species and stable but hazardous organic compounds, such as benzene, thus removing these agents from the airstream. The drying agent, or desiccant, minimizes the quantity of moisture in the airstream as it passes by the activated carbon, which would otherwise coat and render inactive the absorbing surface of the carbon. An ultra low particle absorbing filter layer is also preferably used prior to exhausting the air into the atmosphere.

In one embodiment of the invention, the solution is contained within a separately formed permanent reservoir which is part of the actual filter device or body housing. The solution may be free flowing or alternatively may be soaked into a sponge. In an alternative embodiment, a reservoir is formed within an input line through the filter and is contained in the input line by rupturable membranes. The vacuum flow ruptures the membranes to release the solution for forming a foam. In another embodiment, the reservoir is positioned generally parallel with the airstream, and the action of the airstream draws the solution out of the reservoir. A proper, premeasured amount of solution is contained in the integral reservoir so that a sufficient amount of foam is created without overflow out of the outlet port.

The above and other objectives and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
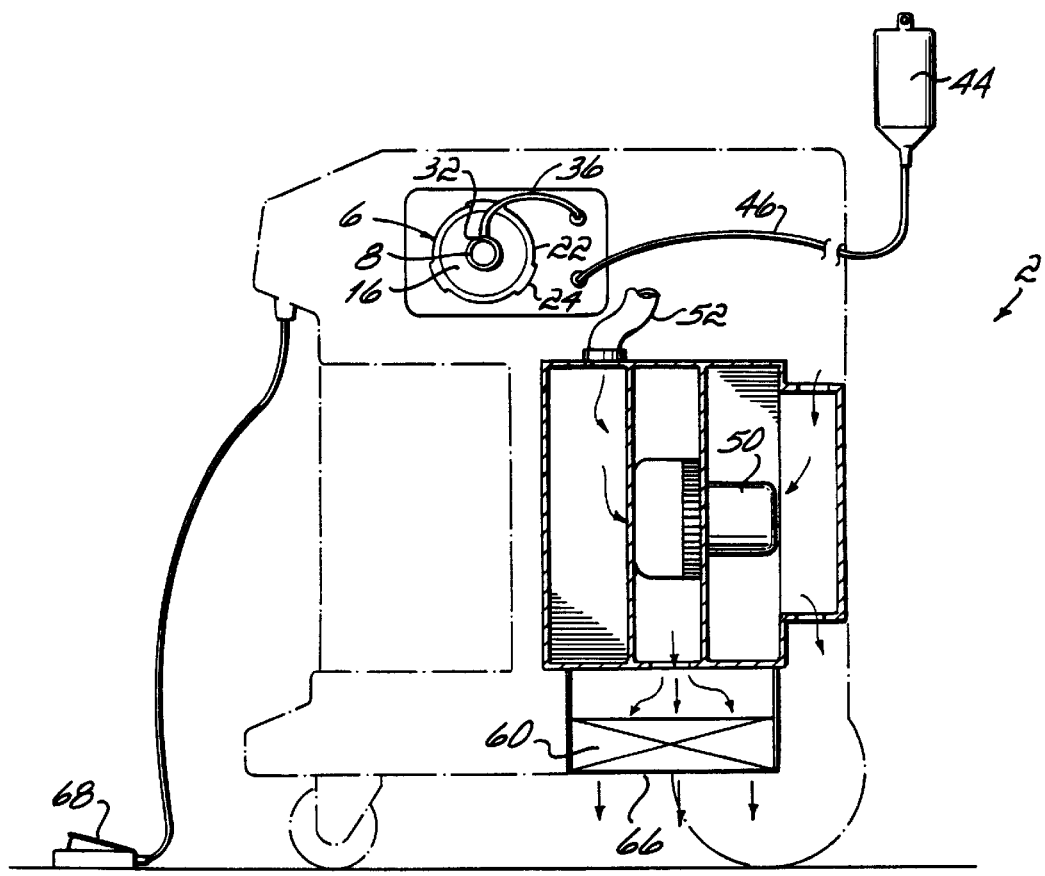
FIG. 1 is a diagrammatic view of the filter cart unit shown in phantom, which houses the filter device and interfacing equipment.

The invention in its broad aspects is adapted to accept an airstream containing gaseous and particulate materials comprising cyanide, formaldehyde, organic compounds, odor-causing species and moisture generated during cauterization or other treatment of animal tissue whereby the apparatus removes the cyanide, formaldehyde, organic compounds, odor-causing species and moisture from the airstream. The apparatus also inactivates bacteria and virus carried along in the airstream. One such apparatus is a filter assembly for receiving and treating an airstream containing gaseous and particulate materials from a surgery plume comprising a canister for retaining a plurality of filter components and having an inlet and an outlet, the inlet for receiving the airstream which contains the gaseous and particulate materials at a rate of flow; introducing means for introducing an aqueous solution comprised of oxidizing and surface active components downstream of the canister inlet; a first porous member downstream of the introducing means for receiving the aqueous solution and the gaseous and particulate materials, adapted to generate a dispersion of the aqueous solution by the interaction of the aqueous solution with the airstream through the porous member; and activated carbon in the canister through which the airstream flows. Good results have been obtained by placing in the canister downstream of the first porous member a second porous member spaced from the first to create a chamber which receives the foam.

As noted above, the surgery plume has been found to contain not only water vapor, hydrogen cyanide, formaldehyde, benzene, odor causing species which typically include additional aldehydes, and particulate matter formed during the burning process, but also bacteria and viruses. Studies have indicated that the HIV virus, among others, has been detected in the surgery plume. Human papilloma virus (HPV) is transmitted in the surgery plume. Thus, it is important not only that the virus component be evacuated from the surgery site, but that it be killed before the evacuated airstream is reintroduced to the environment. In comparing the approximate particle sizes of surgery plume components, bacteria has particle diameters in the range of about 0.2 mm to about 25 microns ($10^{-6}$ meter), and the smoke components of the surgery plume from the laser operation have particles with diameters ranging from about 0.15 to about 8 microns, while the particle diameters of viruses reach a minimum of about 0.05 micron. A container of oxidizing solution through which an airstream is bubbled to remove virus components forms bubbles which are too large in diameter to permit adequate contact of the virus species with the oxidizing solution. It has been found that use of a foam, which is continually being broken down and reformed by the interaction of the airstream with an oxidizing solution containing a surface active component in a defined space, results in sufficient contact time with the bacteria and virus components to kill these species. Alternatively, dispersion in the form of sprays or mists may be employed, but the surface area of the oxidizing solution exposed to the airstream is not as great as the foam in a canister of equal size.

The hydrogen cyanide component of the surgery plume is oxidized by contact with the solution to form cyanate. The formaldehyde as well as any other aldehydes present in the odor causing species become polymerized in the presence of the oxidizing solution as the airstream passes through the foam layer and a Formalex® coated pad.

The benzene component of the surgery plume is resistant to oxidation because of its chemical stability. Nonetheless, it is removed from an airstream by passing that airstream through a layer of activated carbon which absorbs the benzene and other organic compounds. One drawback to the use of activated carbon in the same system with an aqueous solution or a moisture-laden airstream is that the moisture as it passes through the activated carbon tends to deactivate the material and render it unable to remove organic species such as benzene. Thus, it is necessary that a desiccant layer be interposed between the moisture source and the activated carbon layer to optimize the absorption ability of the carbon. So long as the airstream passing through the activated carbon layer is of approximately the same humidity as that of the surgery room, typically in the range of about sixty percent to about eighty percent relative humidity, the level of moisture is sufficiently low to maintain absorption sites on the activated carbon layer to remove the benzene and other organic components.

To provide further assurance that the formaldehyde and other aldehyde components in the surgery plume are removed by the filter device, an optional discrete porous member coated or impregnated with an aldehyde polymerizing agent may be positioned in the filter device.

The odor causing species are removed from the airstream by contact with the oxidizing component in the foam, and are further susceptible to removal as the airstream passes over the desiccant and activated carbon layers, removal being by absorption onto the surface of these layers.

The oxidizing component can be one or a mixture of a number of compounds. Representative materials include but are not limited to sodium hypochlorite, sodium perborate, sodium permanganate, and sodium thiosulfate. The oxidizing agent concentration in the solution is typically in the range of about 0.5 to about 30%, by weight.

The surface active component also can be one or a mixture of a number of compounds. Representative materials include but are not limited to sodium alpha olefin sulfonate, sodium lauryl dimethylamine oxide, nonylphenol polyethylene glycol ether such as TERGITOL NP-10, and disodium oxy-bis dodecyl benzene sulfonate. The surface active component must be essentially inert to the oxidizing agent, yet be capable of contributing to the foam formation of the aqueous solution containing oxidizing agent. The surfactant concentration in the solution is typically in the range of about 1 to about 5%, by weight.

The oxidizing solution is formed by adding the surfactant component to water, then adding the oxidizing agent. The solution maintains optimum long-term stability if the pH is at least about 10.5, typically in the range of about 11.5 to about 12. Where the pH is very alkaline due to the addition of the oxidizing component in the range of 13 to about 14, the pH can be lowered by the measured addition of sodium bicarbonate. The long term stability of the solution will be particularly important in one embodiment of the filter device which comprises an integral solution reservoir therein and eliminates the need for separate delivery of the solution to the filter device during use.

Representative desiccant materials are anhydrous calcium sulfate (4 mesh), amorphous silica and naturally-derived zeolites based on calcium aluminate. Activated carbon is available from Calgon, Inc., Pittsburgh, Pa., in six mesh particle size.

As an alternative to the removal of surgery plume components in a filter device utilizing in part an aqueous oxidizing solution, removal of the cyanide, formaldehyde and benzene components from an airstream has also been effected using a filter assembly without adding oxidizing solution. This assembly comprises a canister for retaining a plurality of filter components and having an inlet and an outlet, the inlet for receiving the airstream containing the gaseous and particulate materials including cyanide, formaldehyde and benzene from the surgery plume at a rate of flow, a filter member inside the canister incorporating a component which is reactive to at least the cyanide component, a discrete desiccant layer inside the canister, a filter member inside the canister incorporating a component reactive to at least the aldehyde component, and a discrete layer of activated carbon for removal of benzene and other organic compounds which is downstream of the desiccant layer. Instead of a foam solution containing oxidizing and surface active components, the dry filter assembly utilizes discrete porous members, such as pads or sponges, coated or impregnated with oxidizing or neutralizing solutions in combination with an aldehyde polymerizing agent incorporated onto a discrete pad, and further retaining the discrete desiccant and activated carbon layers for removal of cyanide, aldehydes, and benzene and other organic compounds. The relative positions of the separate layers is not believed to affect removal capability, except that the carbon layer retains its activity longer if it is downstream of the desiccant layer.

The porous members in the dry filter assembly will include individual members coated or impregnated with compounds which are reactive to components of the surgery plume. These compounds are applied to individual porous members by dipping the members into, or spraying the member with, a solution of the agent, followed by drying. Alternatively, a dry powder containing the agent can be directly applied to the pad.

The amount of compound deposited onto the porous member is a function of the porosity and size of the member, and the concentration of the solution. Aqueous solutions which are reactive to hydrogen cyanide which were used to coat porous members include the following: 20% potassium permanganate; 50% sodium hydroxide; 20% sodium dichloro-s-triazinetrione dihydrate; 45% potassium hydroxide; 10% sodium perborate; and 20% sodium thiosulfate. The alkaline materials listed above coated onto a porous member retained cyanide, but did not convert the cyanide to any extent to a less toxic material. The above percentages are to be considered as representative only. It can be appreciated that other concentration solutions can be used for dipping and spraying. In practice, an amount of agent must be applied which is effective to react with the airstream components over the period of time that the filter assembly is in operation. Because live bacteria and virus are carried into the filter assembly, both with the dry filter assembly and the filter assembly utilizing the oxidizing solution, it is safer practice to dispose of the filter assembly after each use. It has been estimated that presently the maximum amount of time that a laser scalpel is used in a single operation is approximately fifteen minutes. An additional safety factor of about fifteen minutes operating time is built in, resulting in a disposable filter assembly which would be effective in removing the gaseous and particulate materials generated by current laser scalpels for a period of about thirty minutes. As surgical techniques and power levels on lasers and electrocautery knives change, the working lifetime of the disposable filter assembly will need to also be adjusted.

A material reactive to formaldehyde and other aldehydes is available commercially as Formalex®, S & S Company of Georgia, Inc., Albany, Ga. This proprietary material removes the aldehyde component from the airstream by polymerizing the aldehyde. This material applied to a porous member at full strength and then dried was effective in removing formaldehyde from the surgery plume.

In both the wet and dry filter assemblies, minimal head pressure drop is desirable, to permit relatively high airstream flow rates with smaller vacuum units which operate relatively quietly in the operating room environment. The particulate matter in the surgery plume is partially removed as the airstream flows through the multiple porous pads, desiccant and activated carbon layers. However, remaining particulate matter down to a particle size of 0.01 micron may be removed by a separate ULPA (ultra low particle absorbing) filter downstream of the filter assembly, prior to exhausting of the airstream back into the operating room environment. One such ULPA filter is manufactured by Flanders Filters.

Figure 2:
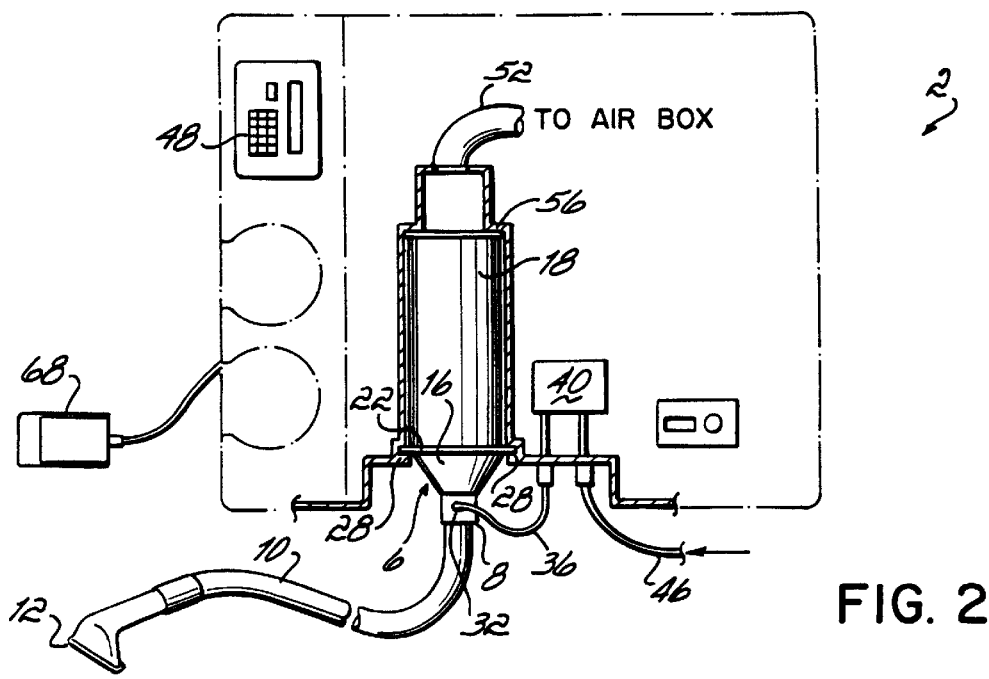
FIG. 2 is a diagrammatic top view of the filter cart unit shown in phantom, housing the filter device.

Referring to the drawings, FIGS. 1 and 2 are schematic views of the filter cart unit 2 which houses the filter assembly 6 and its complementary components. Attached to the inlet port 8 of filter assembly 6 is a flexible hose 10 with a suction tip 12 which is placed near the tissue site where the laser surgery, electrocautery, or other gaseous or particulate generating operation is taking place.

The filter assembly 6 is comprised of a cone portion 16 and a cylindrical portion 18. The cone portion 16 has an inlet port 8 at one end and is permanently attached to the cylindrical portion 18 by adhesive or heat bond, or the like, at the other end. The cone portion 16 has a raised lip 22 with tabs 24 along a portion of the raised lip 22 which fit into and lock with corresponding slots 28 in the filter cart unit 2 to retain the filter assembly 6 in position.

A feed port 32 is located on cone portion 16 at the inlet port 8 to permit introduction of an aqueous solution inside the filter assembly 6. Feed line 36 is attached to feed port 32 and connects with pump unit 40 for supplying a measured portion of oxidizing solution when the wet filter assembly is being used. Pump unit 40 in turn is connected to solution reservoir 44 outside the filter cart unit 2 via supply line 46 for supplying the needed oxidizing solution. Alternatively, the reservoir may be located inside the filter cart unit 2. Acceptable results have been obtained by suspending the solution reservoir 44 above the filter cart unit as in a plastic bag on a support such as an I.V. pole to facilitate proper flow to the pump unit 40 and thereby into the filter assembly 6. The pump unit 40 facilitates uniform, measured introduction of the oxidizing solution into the filter assembly 6, and the solution flow rate is controlled at keypad 48. However, it can be appreciated that other types of methods of fluid introduction can be utilized, even including direct gravity feed from an I.V. bag into the filter assembly 6 via the feed port 32.

Flow rates of oxidizing solution are in the range of about 2.9 to about 7.3 ml/min over the course of the run, and preferably between about 3 and 5 ml/min. As noted, a peristaltic pump such as the Model 54856-070 from VWR Scientific, Philadelphia, Pa., is useful in this application, which can provide the desired solution flow rate by varying the tubing diameter, the cycling time of the pump, or both. For the typical use period of about fifteen minutes, this flow rate provides excellent foam generation without overloading the filter assembly, as evidenced by foam appearing at the filter assembly exhaust.

The suction applied at the surgery site through suction tip 12 is created in a vacuum unit 50 which is connected to the exhaust side of filter assembly 6 through connecting line 52 and gasketed fitting 56. The vacuum unit 50 preferably generates flow rates in the range of about 35 to about 85 standard cubic feet per minute (SCFM), and more preferably between about 55 and about 70 SCFM. A representative vacuum unit is manufactured by Ametek, such as Model No. 116763-13. To minimize back flow from the vacuum unit 50 particularly after the filter assembly 6 has been removed from the cart 2 for disposal, the connecting line 52 is fitted with a flip-up shutter door (not shown) which isolates the air system.

Residual particulates in the airstream from the surgery plume which flow through the components of the filter assembly 6 down to 0.01 micron in size are trapped in the particle filter 60 directly connected to the downstream end of vacuum unit 50. After passage through particle filter 60, the airstream is exhausted to the operating room environment through cart exhaust port 66. Power to the vacuum unit 50 and pump 40 is directly controlled by foot switch 68 or by keypad 48.

Figure 3:
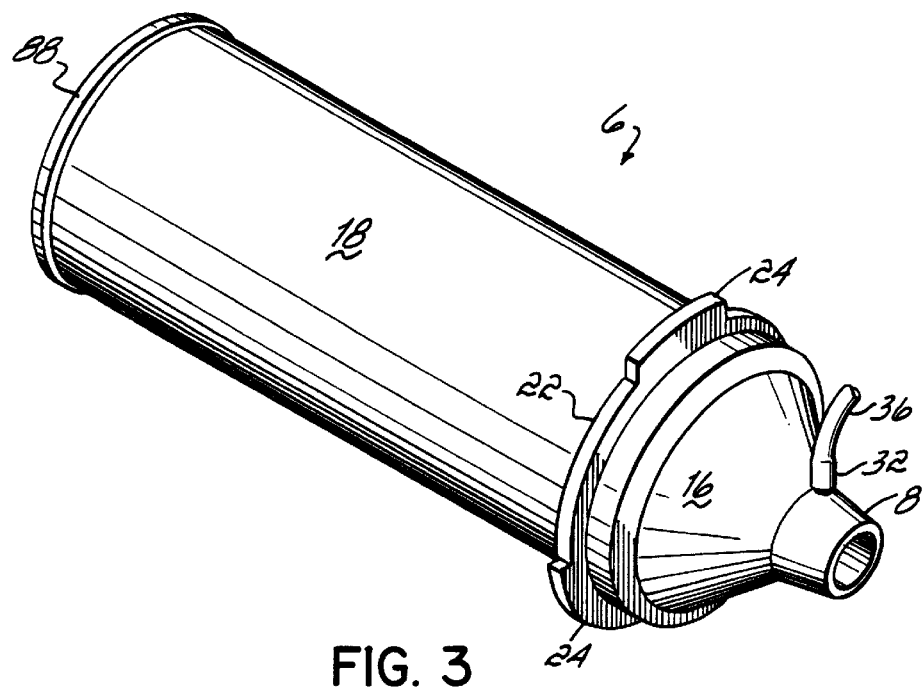
FIG. 3 is a perspective view of the filter device with attached solution inlet line.
Figure 4:
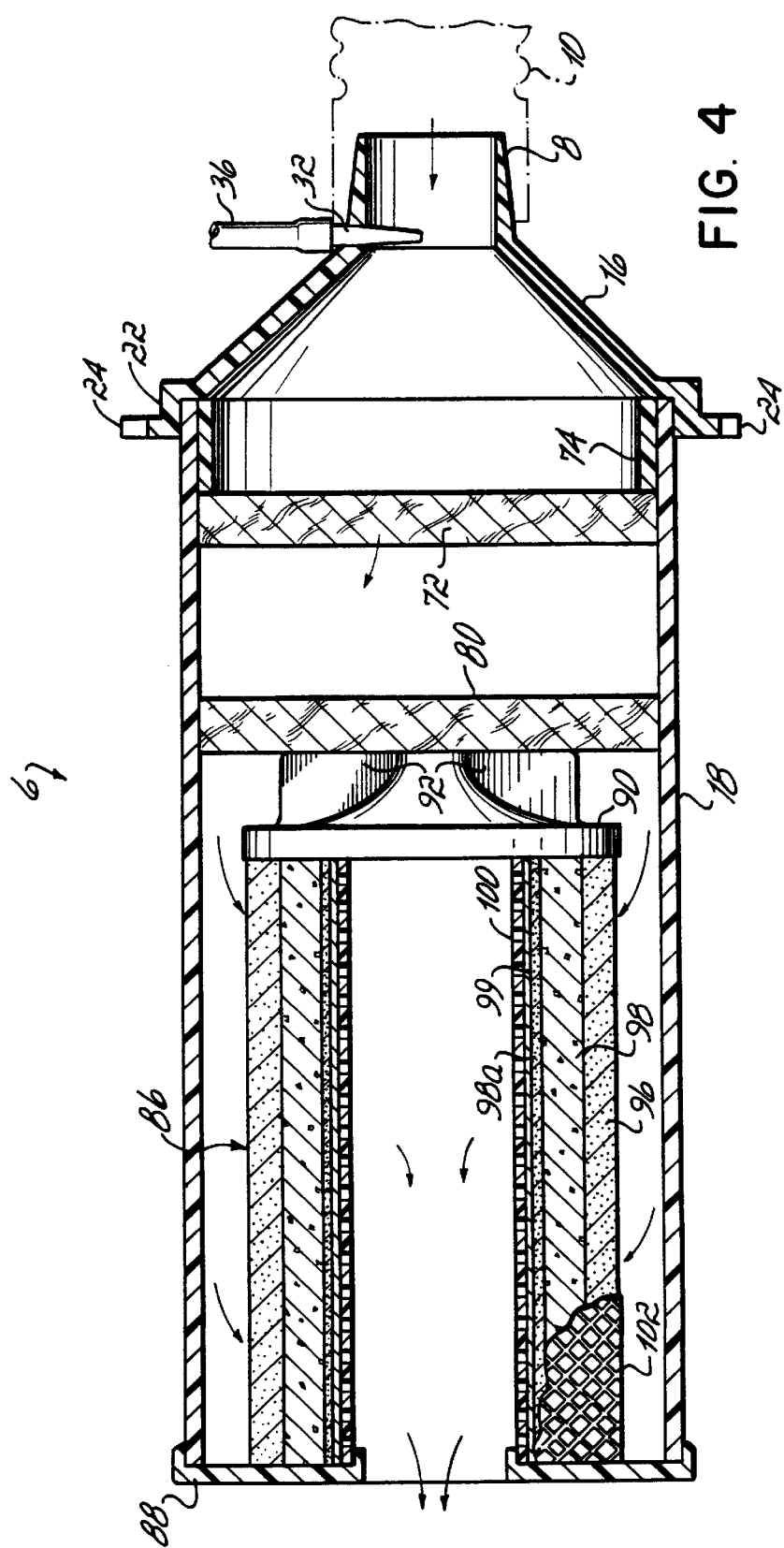
FIG. 4 is a cross-sectional view of the filter device with solution introduction port.

As shown in FIG. 4, the filter assembly 6 receives solution through feed line 36 and feed port 32 which is blown into first dispersal pad 72 by the action of the incoming airstream as indicated by the arrow at inlet port 8. The placement of the tip of feed port 32 should be such as to obtain good dispersion of the solution droplets. The first dispersal pad 72 is porous and is constructed of material inert to the components of the surgery plume and the oxidizing solution. One type of pad is manufactured from a 60:40 blend of nylon and polyester fibers bonded with thermoplastic resin, by Americo, Inc., Atworth, Ga., discussed in more detail below. This pad spans the entire inside diameter of the cylindrical portion 18 of assembly filter 6 to prevent the airstream from bypassing the pad along the inside wall of cylindrical portion 18 and is retained in position by tube spacers 74 on the upstream side and a bead of hot melt adhesive on the upstream side of the pad which contacts both the pad and the inside circumference of the cylindrical portion 18.

Downstream of the first dispersal pad 72 is a second dispersal pad 80. This pad, like first dispersal pad 72, is secured by a bead of hot melt adhesive on the upstream side of the pad. The pad is also manufactured by Americo, Inc. and is discussed in more detail below. This second dispersal pad 80 is coated or impregnated with a formaldehyde reactive component which aids in the formaldehyde removal. An example of such a reactive component is a material sold under the name Formalex®, available from S & S company of Georgia, Inc., Albany, Ga. Formalex® is a proprietary compound which serves to polymerize aldehydes, particularly formaldehyde. Alternatively, the second dispersal pad 80 can be uncoated.

Downstream of the second dispersal pad 80 is a filter cartridge 86 which is secured into the cylindrical portion 18 by a flexible plastisol end cap 88. The filter cartridge 86 has a nose section 90 with a plurality of spacer ribs 92 to deflect air along the side of the filter cartridge 86. The filter cartridge 86 has a tubular construction with an outer layer 96 comprised of a non-woven polyester substrate media impregnated with amorphous silica and serving as a desiccant, such as Lewcott Grade SG-NWPE-4.0-150. The silica is mixed with a polyvinyl acetate adhesive which is then applied to the polyester media. Inside the outer layer 96 is a first carbon tube 98, which is comprised of two wraps of a non-woven polyester substrate media impregnated with activated carbon ground and mixed with a polyvinyl acetate adhesive, such as Lewcott Grade ACF-NWPE-4.0-150. Under the first carbon layer 98 is a second carbon layer 98*a*, which is comprised of coal based powdered activated carbon, regenerated cellulose, cellulosic fiber and latex binder, such as Lydall Grade 703 carbon filter media. Under this layer is a cellulose layer 99, comprised of cellulose media with a trace of polyamide wet strength resin, such as Ahlstrom Grade 1278.

The innermost tube in the filter cartridge 86 is a perforated tube 100 which is injection molded and made from polypropylene, available from Crellin, Inc. As shown in FIG. 4, the entire center length of the filter cartridge 86 is open, which serves as an exhaust conduit for passing the airstream out of the filter assembly 6. Structural support along the outside of the filter cartridge 86 is provided by an outer layer of low density polyethylene extruded netting 102, such as Naltex Grade 407.

The plastisol end cap 88 which retains the filter cartridge 86 inside cylindrical portion 18 of filter assembly 6 is ring-shaped and secures to the polypropylene perforated tube of the filter cartridge 86 and the outside surface of the cylindrical portion 18 by a bead of adhesive around the entire circumference of cylindrical portion 18. The plastisol material is a colloidal dispersal of a vinylchloride resin and a plasticizer which is FDA approved for use in potable water applications, such as Dennis Chemical Grade 9233-40. This plastisol end cap 88 is sealingly connected to the vacuum unit 50 from which the suction creating the airstream flow through filter assembly 6 is generated. The filter assembly 6 is shown as a discrete unit in FIG. 3.

Figure 5:
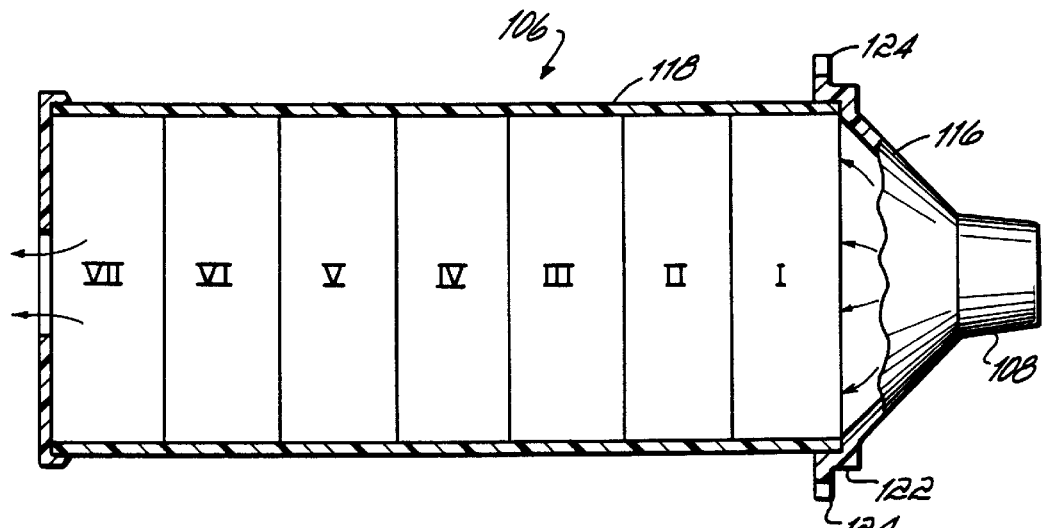
FIG. 5 is a cross-sectional side view of an alternative filter device application.

An alternative filter assembly removes cyanide, formaldehyde and other aldehydes and benzene from an airstream without the use of a separately introduced oxidizing solution. As shown in FIG. 5, filter assembly 106 has an inlet port 108 for receiving a flexible hose, such as the hose 10 shown in FIG. 1. The filter assembly 106 is comprised of a cone portion 116 and a cylindrical portion 118. On cone portion 116 is a raised lip 122 at the point of friction fit connection to the cylindrical portion 118. On this raised lip 122 are a plurality of tabs 124 for mating with slots, such as those shown in FIG. 1 as slots 28.

Inside the cylindrical portion 118 are a variety of spaces for receiving various spacer members, reactive members, and absorptive materials. One material which has been used both as a spacer pad to hold a position in the cylindrical portion, help disperse the airstream, and to serve as the substrate for one or more chemical coatings to render the pad reactive is a 60/40 nylon/polyester composite with a thermoplastic resin as a bonding agent, such as that manufactured by Americo, Inc. The spaces within the filter assembly in FIG. 5, designated I–VII, are filled with layers of desiccant, activated carbon, impregnated or coated pads, and uncoated spacer pads in different configurations. Where desired, one or more spaces can be left empty. The pads are secured in the filter assembly 106 by a bead of hot melt glue around the inside diameter of the cylindrical portion 118. The spaces I–VII are filled with a pad coated or impregnated with a neutralizing or oxidizing agent to remove cyanide, a pad with an aldehyde-removing agent, such as Formalex®, and a layer of activated carbon to remove benzene and other organic compounds. Typically, a layer of desiccant is placed within the cylindrical portion 118 upstream of the activated carbon layer. Spacer pads with no coating are used to separate and maintain the position of the desiccant and activated carbon layers and to help disperse the airstream, where desired.

In a typical configuration, from the upstream end, (I) is a porous uncoated pad, followed by a porous pad coated with sodium hydroxide solution and dried (II), a porous pad coated with Formalex® (III), a layer of desiccant (IV), a spacer pad (V), a layer of activated carbon (VI) and a final spacer pad (VII).

Because the major component of the laser plume is water vapor, there is a risk that moisture levels can rise within the filter assembly 106 to a point where any activated carbon therein loses its activity. Thus, to maximize the absorption time of any activated carbon, it is preferred that a desiccant layer be located upstream of any activated carbon. It has been found that good results can be obtained with the activated carbon at the downstream end of the filter assembly 106, with the desiccant directly upstream. However, it is believed that acceptable results can be obtained even where activated carbon is located near the upstream end of the filter assembly 106. Where the period of moisture buildup is relatively short, the activated carbon layer can be used without the benefit of an upstream desiccant layer. However, as expected, the working lifetime of the activated carbon is shortened.

Operating Examples

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

A filter assembly of the type shown in FIG. 4 was constructed having a cylindrical portion 18 with a ten inch length and four inch inside diameter and made from clear polyvinyl chloride to permit viewing of the filter assembly components. Inside the assembly was an uncoated first dispersal pad 72 and a second dispersal pad 80 coated with Formalex®. The first dispersal pad was one inch thick and four inches in diameter and made from a nonwoven nylon/polyester blend such as that used for manufacturing industrial floor scrubbing pads. This particular pad material was manufactured by Americo, Inc., Atworth, Ga., and has been used in both wet and dry filter assemblies as a dispersal and spacer pad and as a substrate for an agent reactive to cyanide. The nylon fiber component of this pad has a 60 denier. The polyester fiber components have a range of deniers of 45, 50, 100 and 300. The pad material when used in its scrubbing application is identified as the True Grit™, green cleaner pad. The second dispersal pad 80 was also obtained from Americo, and the commercial product is identified as the True Grit™ tan buff pad. The nylon fiber component has a 60 denier. The polyester fiber components have deniers of 25, 45, 50 and 60. This second pad was also one inch thick and four inches in diameter, and coated with Formalex®, having a total dried weight of 8.0 grams. This pad was typically used as the substrate for the Formalex® coating.

An aqueous oxidizing solution of 2.5% sodium lauryl dimethylamine oxide (30% active), 2.5% sodium alpha olefin sulfonate (40% active) and 10% sodium hypochlorite (9.5% active) with the pH adjusted to about 11 by addition of sodium bicarbonate was introduced through feed port 32 at a rate of about 5.5 ml/min over the course of the run. The airstream was conducted into the filter assembly at a flow rate of about 60 SCFM. In a first run, the airstream was injected with *E. coli* colonies and nutrient to produce a concentration upstream of the filter of about 2.6 billion colonies/min. over a fifteen minute period. In a second run, the airstream was injected with *Serratia marcescens* and nutrient to produce an upstream concentration of almost one billion colonies/min. over a fifteen minute monitoring period.

After about one minute of operation in both runs, it was observed that the foam generated in the space between the first and second dispersal pads was relatively coarse. Foam was also forming downstream of the second dispersal pad between the inner wall of the cylindrical portion 18 and the outer layer 96 of filter cartridge 86. This foam had a much finer bubble structure, with the consistency of a shaving cream. No foam or visible moisture escaped from the filter assembly during the runs.

Analysis of the airstream exhausted through the filter assembly showed no detectable living bacteria. A series of control runs utilizing the same bacteria in the same concentration without the filter showed substantial amounts of detected living bacteria colonies.

A dry filter assembly as generally shown in FIG. 5 was constructed from a Kraft paper-wrapped tube with a white paper outer layer and an inner coating of paraffin wax. As with the wet filter assembly, the paper tube cylindrical portion 18 had a four inch inside diameter and a ten inch length. The following table shows the removal ability of various configurations of filter components against certain materials typically found in surgery plume. The pads were secured inside the cylindrical portion 18 by a continuous bead of hot melt adhesive on the upstream side.

TABLE 1

| Run | Plume Component Monitored | Filter Configuration | | Component Concentration (PPM) | |
|---|---|---|---|---|---|
| | | | | Pre-filter | Post Filter |
| | | | | (Sampling every 2 min.) | |
| 1 | Hydrogen Cyanide | I | Open Cell Urethane Sponge | | |
| | | II | Green Pad (uncoated) | 1. 7 | <2 |
| | | III | Buff Pad w/Formalex ® | 2. 3.5 | 2 |
| | | IV | Anhyd. CaSO₄ | 3. 5 | <2 |
| | | V | Green Pad (uncoated) | 4. 7 | N.D. |
| | | VI | Activated Carbon | | |
| | | VII | Green Pad (uncoated) | | |
| | | | | (Sampling every 5 min.) | |
| 2 | Formaldehyde | I | Green Pad (uncoated) | | |
| | | II | Buff Pad w/Formalex ® | 1. 15 | N.D. |
| | | III | Green Pad (uncoated) | 2. >25 | 4.5 |
| | | IV | Zeolite (Ca Aluminate) | 3. 15 | 1.5 |
| | | V | Green Pad (uncoated) | 4. >15 | 4 |
| | | VI | Activated Carbon | 5. 20 | 3 |
| | | VII | Green Pad (uncoated) | | |
| | | | | (Sampling every 2 min.) | |
| 3 | Smoke/ Odor | I | Green Pad w/NaOH | Smoke was reduced; | |
| | | II | Green Pad (uncoated) | Odor not substantially affected | |
| | | III | Zeolite (Ca Aluminate) | | |
| | | IV | Green Pad (uncoated) | | |
| | | V | Activated Carbon | | |
| | | VI | Activated Carbon | | |
| | | VII | Green Pad (Uncoated) | | |
| 4 | Hydrogen Cyanide | I | Green Pad w/NaOH | 1. >60 | 26 |
| | | II | Green Pad w/NaOH | 2. 58 | 30 |
| | | III | Buff Pad w/Formalex ® | 3. 47 | 20 |
| | | IV | Zeolite (Ca Aluminate) | 4. 45 | 22 |
| | | V | Green Pad (uncoated) | | |
| | | VI | Activated Carbon | | |
| | | VII | Green Pad (uncoated) | | |

The wet filter assembly having the filter cartridge 86 positioned therein has been found to be effective in achieving excellent contact time with the surgery plume component by increasing significantly the surface area through which the surgery plume must pass with minimum drop in the head pressure across the filter assembly. It is estimated that the head pressure drop in this filter assembly is approximately only three percent.

In contrast, testing has been conducted on a hybrid filter assembly having the internal configuration similar to the dry filter, but with injection of an oxidizing solution as in the wet filter. Good results were obtained as to removal of certain particulates, odor-causing species, moisture, and cyanide, formaldehyde, and benzene. However, the reactive agents coated onto the porous pad or sponge tended to become blinded by the volume of fluids inside the filter assembly, which increased the head pressure drop, and in time decreased the filtering efficiency.

Maximum efficiency in removing the odor-causing species from the surgery plume is observed with the wet filter assembly. Though the concentration of suspected carcinogenic/mutagenic agents in a surgery plume can be substantially decreased using the dry filter assembly, residual odor does carry through.

Figures 6, 6A, 6B:
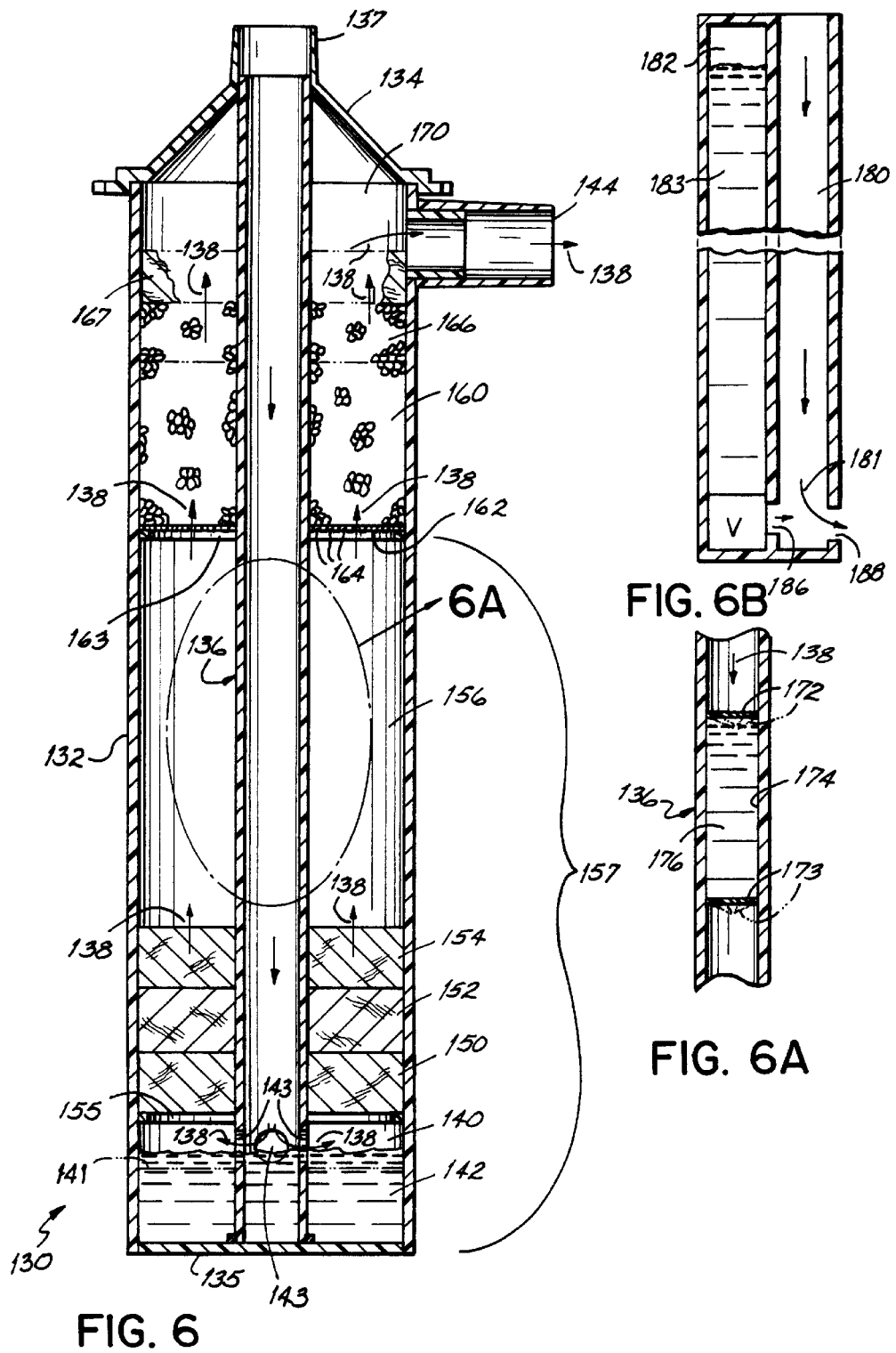
FIG. 6 is a cross-sectional view of an embodiment of the filter device with an integral solution reservoir therein.
FIG. 6A is an enlarged cross-sectional view of a portion of FIG. 6 showing an alternative embodiment of the solution reservoir; and, FIG. 6B is a cross-sectional view of an alternative embodiment of the solution reservoir.

FIG. 6 illustrates an alternative embodiment of the filter device of the invention which comprises an integrally formed solution reservoir which contains the oxidizing and surface active solution therein to eliminate the need for a separate solution supply and delivery system. The solution contained within the solution reservoir of the filter device is automatically engaged by the airstream passing through the filter device when a vacuum is drawn. Accordingly, the solution and intercepting airstream impinge upon dispersal pads to continually form and breakdown a foam within the filter device for reducing and eliminating mutagenic and carcinogenic agents, odor causing species, and bacteria and virus within the surgery plume component of the air stream.

The filter device or assembly 130 of the invention comprises a generally body 132 sealed on one end by a cylindrical cap 134 and at the other end by an end wall 135. The body 132, cap 134 and end wall 135 are all sealed in a fluid-tight relationship to contain the foam. One suitable material for these components is polyvinylchloride. The filter assembly 130 further comprises an airflow input line 136 for introducing the airflow containing the surgery plume component into the assembly for filtering. The airflow input line 136 includes an inlet port 137 which is operably coupled to a flexible hose and suction tip assembly (not shown) which is discussed hereinabove and is placed near the tissue site where the laser surgery or other surgery occurs to draw up the surgery plume created by such surgery. As illustrated and discussed further below, the input line 136 defines a section of the airstream passage which provides filtering of the surgery plume. The air flows in line 136 in the direction of arrows 138. Opposite the inlet port 137, the line 136 intersects a solution reservoir 140 integrally formed inside the body 132 which contains an amount or charge of solution 142 for forming the foam. The foam is caused by the airstream and solution mixture impinging upon a plurality of dispersal pads 150, 152, 154. The solution is similar to the oxidizing and surface active solution discussed hereinabove with respect to other embodiments of the invention.

Openings 143 are formed in the end of the input line 136 so that an air flow introduced into the line in the direction of 138 will travel out of the openings 143 to engage the solution 140 and create a foam as illustrated. The airstream flows in the direction of arrows 138 down through the line 136 and then back up through the filter assembly 130 to exit out through an outlet port 144 positioned on the body 132 proximate inlet port 137. Essentially, little filtering of the surgery plume occurs within the airflow passage or airflow input line 136 although some foam may form in line 136. Rather, most filtering occurs-after the airflow has exited the openings 143 and is then drawn back up and out of the filter assembly through the outlet or exhaust port 144. Accordingly, the outlet port 144 is coupled to an appropriate vacuum unit (see FIG. 1) which will preferably generate flow rates in the range of 35 to 85 (SCFM) as discussed in greater detail hereinabove. Since the airstream is directed to one end of the assembly 130 to flow back toward the inlet port 137, the outlet port 144 may be located proximate the inlet port 137. The flow of air back to the outlet port 144 from openings 143 defines the remaining section of the airstream passage defined by assembly 130 and illustrated by airflow arrows 138.

In an alterantive emobidment of the invention, a solution-soaked sponge 141 may be utilized with reservoir 140 to contain the solution. The action of the airstream through the sponge 141 further acts to create the foam.

Turning now to the other filtering components of the filter assembly 130, the plurality of dispersal pads 150, 152 and 154 are positioned in the filter assembly 130 above the solution reservoir 140, or in effect, downstream from the solution reservoir. During operation of the filter assembly 130, the solution 142 is essentially blown around and into the first dispersal pad 150 by the action of the incoming intercepted airstream indicated by the arrows 138 at openings 143. Thus, a foam is formed. The first dispersal pad 150 is porous and is constructed of material which is generally inert to the components of the surgery plume and the oxidizing solution. One such pad is a blend of nylon and polyester fibers bound with a thermoplastic resin and available from Americo, Inc., Atworth, Ga., as discussed hereinabove. Pad 150 generally spans the entire inside diameter of the cylindrical body 132 and is retained in a position above the solution reservoir 140 by an annular lip 155 which extends around the inside diameter of body 132. Lip 155 is configured so as not to substantially hinder progression of the foamed solution up into other areas of the filter. The first dispersal pad 150 might also be secured by a bead of hot melt adhesive.

In the embodiment illustrated in FIG. 6, another dispersal pad 152 is positioned generally stacked on the first dispersal pad 150, but further downstream from dispersal pad 150. The dispersal pad 152 in the embodiment illustrated in FIG. 6 is essentially the same as dispersal pad 150 and is also available from Americo, Inc. As will be appreciated, the multiple stacked dispersal pads 150, 152 might also be replaced by a single dispersal pad to accomplish similar dispersion and foaming of the oxidizing solution. In one embodiment, the pads are approximately the diameter of body 132 and are 1 inch or 2.54 cm thick.

Dispersal pad 154 is also a nylon-polyester blend available from Americo, Inc. under the commercial name True Grit™ tan buff pad. Dispersal pad 154 rests generally on top of, and downstream from, dispersal pad 152 and may be secured by a bead of hot melt adhesive (not shown). Dispersal pad 154 is coated or impregnated with a formaldehyde reactive component which aids in the removal of formaldehyde from the surgery plume. One suitable example of such a reactive component is a material sold under the name Formalex® which is discussed hereinabove. Formalex® serves to polymerize aldehydes, particularly formaldehyde. As will be appreciated, one or more of the other dispersal pads 150, 152 might also be coated or impregnated with a neutralizing or oxidizing agent to remove cyanide as discussed hereinabove.

When the solution 142 is blown around and against the layers of dispersal pads 150, 152, 154, a foam is created. The foam has the desired compostiion and bubble size due to the interaction between the airstream, solution, and pads. The foam is generally contained within reservoir 140, within the pads, and within a foaming chamber 156 positioned above the pads or generally downstream from the pads with reference airstream passage defined by arrows 138. In other words, the oxidizing solution foam exists in the area of filter assembly 130 generally indicated by bracket 157. Most of the foam will generally be confined outside of line 136 although some may exist inside the line. As discussed, the foam is suitable for reducing and eliminating mutagenic and carcinogenic agents and odor causing species and is further active to kill bacteria and virus in the surgery plume.

The intercepted airstream, the solution reservoir and the pads are all operably interactive to form and break down a foam inside filter body 132. The foam is continually formed and broken down as it filters the airstream and surgery plume. The filter body is configured as described to contain the foam and expose the airstream and surgery plume to the foam for a time period sufficient to effect removal of gaseous and particulate materials from the surgery plume airstream to cleanse the airstream to be exhausted to the atmosphere. The composition of the foam created by the pads and solution is very effecitve in filtering the airstream. The containment of the solution 142 within the integral solution reservoir 140 eliminates the need for a separate solution supply and accompanying delivery system. Therefore, the filter device illustrated in FIG. 6 may be utilized with a variety of different filter carts and evacuation units without any need for retrofitting either the cart or the filter device. The filter device may be easily and efficiently installed in-line with a vacuum line and will automatically produce the necessary foam because the vacuum airstream 138 intercepts reservoir 140 and directs solution into pads 150, 152 and 154. Additionally, a manufacturer or distributor does not have to carry a large number of different filter devices to be used with different filter carts and evacuation units. This increases the profitability of the filter device and reduces the complexity of the manufacturing equipment necessary for producing the filter device.

Physically above the foaming area as illustrated in FIG. 6, but downstream thereof, the filter assembly 130 further comprises a layer of moisture absorbing material or desiccant 160 which is separated by the foaming area 157 by a screen plate 162 held in place by an appropriate annular lip 163 positioned around the inside of the cylindrical body 132. Screen plate 162 includes a plurality of openings 164 which allows the airstream to flow therethrough, again as indicated by arrows 138. The desiccant layer 160 absorbs moisture from the airstream as it passes out of the foaming region 157. A layer of activated carbon 166 is positioned downstream from the desiccant layer 160 and is active to remove benzene and other organic components from the airstream 138. Moisture within the air stream is detrimental to the activated carbon because it tends to deactivate the material and render it unable to remove organic species such as benzene. Therefore, the desiccant layer 160 provides a level of moisture in the airstream which is sufficiently low to maintain absorption sites on the activated carbon layer 166 to remove the organic components. In accordance with one embodiment of the invention, the desiccant layer may be approximately in the range of 1/16 to 2 inches or 1.5 mm to 5 cm thick and the activated carbon layers is approximately in the arnge of ¼ to 2 inches or 6.3 mm to 5 cm thick. As will be appreciated by a person of ordinary skill in the art, various other thicknesses of the different layers within the filter assembly 130 may be utilized in accordance with a particular filtering application.

In the embodiment of the invention illustrated in FIG. 6, an ULPA (ultra low particle absorbing) filter 167 is placed downstream of the carbon layer 166 for removing particulate matter down to a particle size of 0.01 micron as discussed.

Further downstream, an exhaust chamber 170 receives the airstream 138 passing through the activated carbon layer 166. Outlet port 144 is coupled to the exhaust chamber 170 and thus draws the filtered and cleansed airstream out of the filter assembly to be further exhausted as discussed hereinabove.

The amount of oxidizing solution 142 contained within solution reservoir 140 is premeasured for the particular application and would generally depend upon the length of time of the surgery plume for which the filter is used, which, at a maximum, is generally approximately 15 minutes. A sufficient amount of solution 142 must be present in reservoir 140 to maintain the foam which operates in accordance with the principles of present invention by continually being broken down and reformed through the interaction of the intercepted airstream with the solution in a defined space. The foam provides a maximized surface area exposure of the solution to the airstream for efficient and generally rapid reduction of the undesirable surgery plume agents within the airstream. Furthermore, the amount of solution 142 is maintained so that good foam generation is achieved without overloading the filter assembly, as will be evidenced by foam appearing at the filter assembly exhaust chamber 170 and outlet port 144.

The filter assembly 130 provides a foam with increased surface area to provide increased effective contact time with the surgery plume component of the air stream. This is achieved without a substantial drop in the vacuum pressure across the filter assembly. Therefore, a good flow rate is achieved through the filter assembly 130 of the invention.

FIG. 6A illustrates an alternative embodiment of the filter assembly 130 of the invention wherein the fluid reservoir might be integrally contained within the air input line 136. More particularly, the input line 136 may include rupturable opposing membranes 172, 173 which define the solution reservoir 174 therebetween. The solution reservoir 174 contains the oxidizing solution 176 for creating a foam within the filter assembly 130. Upon coupling filter assembly 130 to an evacuation unit and drawing a vacuum in the filter assembly, air flow in the direction of arrow 138 is produced to intercept reservoir 174. The membranes 172, 173 are constructed to be rupturable so that upon impingement by the air flow 138 they rupture and release the solution 176 into the filter assembly. One preferable material for the rupturable membranes 172, 173 is Gore-Tex® material. In that way, the solution 176 is contained and is not subject to spill or leak from the filter assembly 130 when it is transported or installed. As may be appreciated, the fluid reservoir or solution reservoir 174 is indicated as being located within the input line 136 proximate the foaming chamber 156. However, solution reservoir 174 may also be located generally anywhere along the length of the line 136.

FIG. 6B illustrates another alternative embodiment of the invention in which the solution reservoir is positioned alongside and generally parallel the introduced airstream. That is, the airstream inflow passage 180 directs an airstream 181 past sealed reservoir 182 full of solution 183. The airstream 181 acts to draw solution 183 through an appropriate valve 186. The valve 186 monitors the flow rate of the solution into the airstream 181, and the combined solution 183 and airstream 181 exit through an opening 188 to impinge upon dispersal pads in accordance with the principles of the invention. The integral reservoir 182 contains the proper amount of solution for the filter.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A filter device for treating an airstream containing gaseous and particulate materials from a surgery plume comprising:

an elongated filter body having an inlet port positioned proximate a first end of the body and an outlet port also positioned proximate the first end of the body and the inlet port, an airstream passage extending between the inlet and outlet ports for accepting and exhausting the surgery plume airstream, the airstream passage proceeding from the inlet port along the body to an endwall at a second end of the body and then reversing direction and proceeding back along the body to the outlet port;

an internal solution reservoir formed inside the filter body and positioned in-line with the airstream passage, the reservoir positioned proximate the endwall at the second end of the body to fill a portion of the passage for intercepting the airstream before it proceeds back to the outlet port;

a charge of a reactive solution being contained within said reservoir;

the intercepted airstream and the reactive solution operably interactive for forming and breaking down a foam inside the filter body;

at least one dispersal pad positioned in the airstream passage between the solution reservoir and the outlet port, the dispersal pad configured for operably engaging the airstream and reactive solution for forming and breaking down the foam, the filter body configured to contain the foam and expose the airstream to the foam for a time period sufficient to effect removal of gaseous and particulate materials from the surgery plume airstream;

whereby the filter device exhausts the treated airstream into the atmosphere through the outlet port generally cleansed of agents in the surgery plume.

2. The filter device of claim 1 wherein said at least one dispersed pad comprises a plurality of dispersal pads downstream of the solution reservoir, the dispersal pads configured for operably engaging the airstream and reactive solution for forming and breaking down the foam.

3. The filter device of claim 1 wherein the dispersal pad is treated with a reactive component operable for removing aldehydes from the airstream.

4. The filter device of claim 1 wherein the dispersal pad is treated with a reactive component operable for removing cyanide from the airstream.

5. The filter device of claim 1 further comprising a foaming chamber positioned in the filter body downstream in the airstream from the dispersal pad for capturing the foam.

6. The filter device of claim 1 further comprising a layer of activated carbon positioned in the filter body downstream in the airstream passage from the solution reservoir for removing organic compounds from the surgery plume airstream.

7. The filter device of claim 6 further comprising a layer of moisture absorbing material positioned in the filter body upstream in the airstream passage from the activated carbon layer for removing moisture from the airstream before the airstream enters the activated carbon layer.

8. The filter device of claim 1 further comprising an ultra low particulate absorbing layer positioned in the filter body downstream in the airstream passage from the solution reservoir for removing particles from the airstream.

9. The filter device of claim 1 wherein the airstream passage further comprises an airflow input line for directing an airstream into the filter body, the solution reservoir integrally formed within the airflow input line for intercepting the airstream.

10. The filter device of claim 9 wherein the solution reservoir comprises at least one rupturable membrane engaging a surface of the line and containing the solution, the membrane operable to rupture when the reservoir is intercepted by the airstream for releasing the solution to form a foam.

\* \* \* \* \*